(12) United States Patent
Cremer et al.

(10) Patent No.: US 8,318,631 B2
(45) Date of Patent: Nov. 27, 2012

(54) PROCESS FOR PREPARING A CATALYST CONSISTING OF A SUPPORT BODY AND A CATALYTICALLY ACTIVE COMPOSITION APPLIED ON THE SURFACE OF THE SUPPORT BODY

(75) Inventors: Ulrich Cremer, Mannheim (DE);
Andreas Raichle, Ludwigshafen (DE);
Frank Rosowski, Mannheim (DE);
Ulrich Hammon, Mannheim (DE);
Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 741 days.

(21) Appl. No.: 12/039,231

(22) Filed: Feb. 28, 2008

(65) Prior Publication Data
US 2008/0214863 A1 Sep. 4, 2008

Related U.S. Application Data

(60) Provisional application No. 60/892,419, filed on Mar. 1, 2007.

(30) Foreign Application Priority Data

Mar. 1, 2007 (DE) .......................... 10 2007 010 422

(51) Int. Cl.
C07C 51/16 (2006.01)
B01J 23/00 (2006.01)
(52) U.S. Cl. ......................... 502/312; 562/535; 562/546
(58) Field of Classification Search .................. 562/546, 562/535; 502/178, 312
See application file for complete search history.

(56) References Cited

U.S. PATENT DOCUMENTS

| 4,259,211 | A | * | 3/1981 | Krabetz et al. | ................ 502/178 |
| 5,637,546 | A | | 6/1997 | Tenten et al. | |
| 5,677,261 | A | | 10/1997 | Tenten et al. | |
| 5,910,608 | A | | 6/1999 | Tenten et al. | |
| 6,169,214 | B1 | | 1/2001 | Tenten et al. | |
| 6,794,539 | B2 | | 9/2004 | Unverricht et al. | |
| 7,115,776 | B2 | | 10/2006 | Hammon et al. | |
| 2004/0245681 | A1 | | 12/2004 | Dieterle et al. | |
| 2004/0249183 | A1 | | 12/2004 | Dieterle et al. | |
| 2005/0065370 | A1 | * | 3/2005 | Borgmeier et al. | ........... 562/546 |
| 2005/0096483 | A1 | | 5/2005 | Dieterle et al. | |
| 2005/0261517 | A1 | | 11/2005 | Dieterle et al. | |
| 2006/0201573 | A1 | | 9/2006 | Petzoldt et al. | |
| 2006/0205978 | A1 | | 9/2006 | Yunoki et al. | |
| 2008/0187467 | A1 | | 8/2008 | Dieterle et al. | |

FOREIGN PATENT DOCUMENTS

| DE | 102 32 748 | 7/2002 |
| DE | 10 2004 025 445 A1 | 2/2005 |
| DE | 103 50 822 A1 | 6/2005 |
| DE | 10 2005 010 645 A1 | 8/2005 |
| EP | 0 614 872 A1 | 9/1994 |
| EP | 0 714 700 A2 | 6/1996 |
| EP | 0 990 636 A1 | 4/2000 |
| EP | 1 106 598 A2 | 6/2001 |
| WO | WO 95/11081 | 4/1995 |
| WO | WO 02/24327 A1 | 3/2002 |
| WO | WO 2004/108267 A1 | 12/2004 |
| WO | WO 2004/108284 A1 | 12/2004 |

* cited by examiner

Primary Examiner — Taylor Victor Oh
(74) Attorney, Agent, or Firm — Oblon, Spivak, McClelland, Maier & Neustadt, L.L.P.

(57) ABSTRACT

A process for preparing a coated catalyst in which a finely divided mixture of a multielement oxide comprising the elements Mo and V and a molybdenum oxide or a molybdenum oxide former is applied to the surface of a support body as an active composition.

10 Claims, 3 Drawing Sheets

PROCESS FOR PREPARING A CATALYST CONSISTING OF A SUPPORT BODY AND A CATALYTICALLY ACTIVE COMPOSITION APPLIED ON THE SURFACE OF THE SUPPORT BODY

Figure 1:
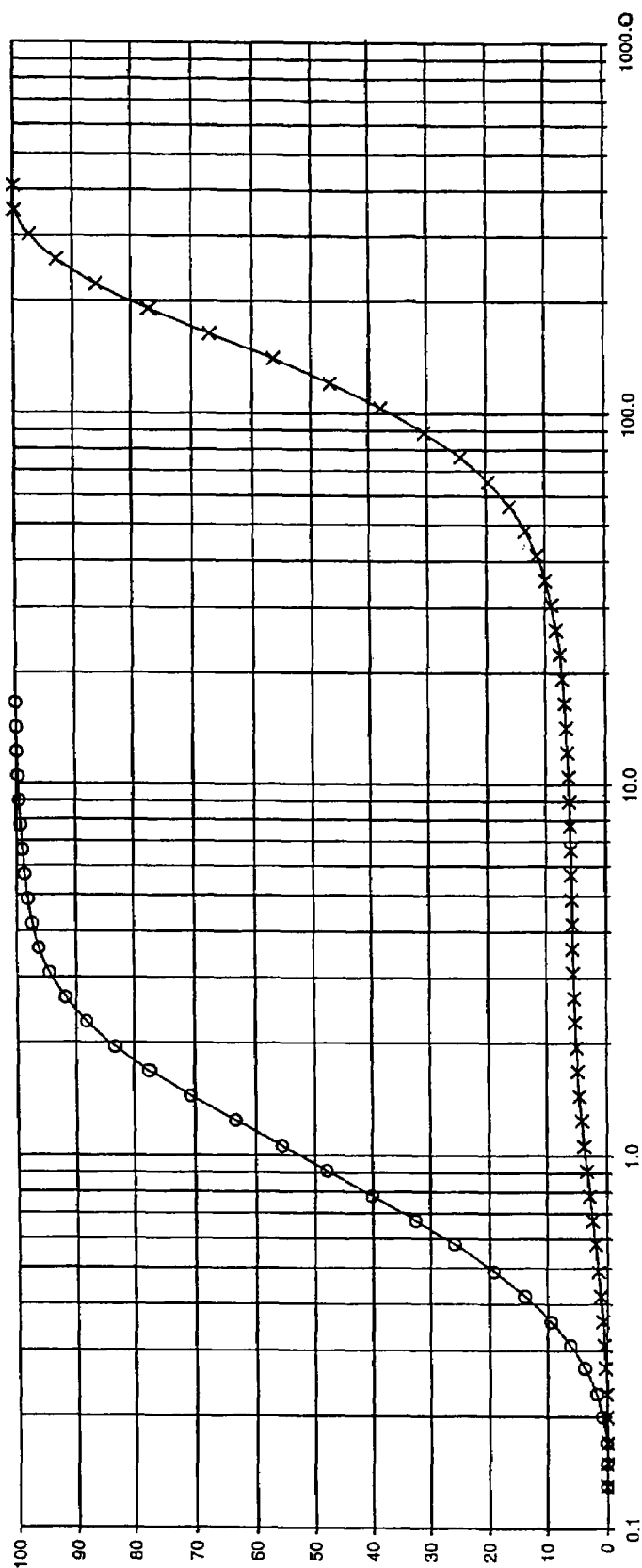
FIG. 1: Particle diameter distribution (volume fraction versus diameters (μm) on a logarithmic scale) determined for MoO3 from Climax Molybdenum Marketing Corporation.
Determination according to ISO 1332.
x: distribution for the commercial product
o: distribution for the primary particles of the commercial product

The present invention relates to a process for preparing a catalyst (a coated catalyst) consisting of a support body and a catalytically active composition applied on the surface of the support body, in which the active composition is attached to the surface of the support body with the aid of a binder.

Processes for preparing coated catalysts of the type described above are known (cf., for example, WO 95/11081, WO 2004/108267, WO 2004/108284, US-A 2006/0205978, EP-A 714700 and DE-A 102005010645).

The active composition is, in a large number of cases, a multielement oxide comprising the elements Mo and V. The expression "multielement oxide" expresses that the active composition comprises, as well as Mo, V and O (oxygen), also at least one further chemical element.

The molar proportion of the element Mo in the total amount of all elements other than oxygen in the catalytically active multielement oxide composition is generally from 5 to 95 mol %, frequently from 10 to 90 mol % and in many cases from 15 to 85 mol % or from 20 to 80 mol %. The molar ratio of Mo present in the catalytically active multielement oxide composition to V present in the catalytically active multielement oxide composition, Mo/V, is typically from 15:1 to 1:1, frequently from 12:1 to 2:1.

Catalysts of the above-described type are suitable in particular for the catalysis of the heterogeneously catalyzed partial gas phase oxidation of acrolein to acrylic acid.

DE-A 10350822 and DE-A 102004025445 disclose that such a process for heterogeneously catalyzed gas phase partial oxidation of acrolein to acrylic acid can be conducted essentially continuously over prolonged periods over one and the same fixed catalyst bed.

However, the fixed catalyst bed loses quality in the course of the operating time. In particular, its activity deteriorates.

In order to be able to operate the fixed catalyst bed, whose manufacture and exchange are comparatively inconvenient and costly, for as long as possible in a reactor charged with it in spite of this, attempts are made in the prior art to counteract the aging process of the fixed catalyst bed in a wide variety of different ways.

EP-A 990636 (for example page 8 lines 13 to 15) and EP-A 1106598 (for example page 13 lines 43 to 45) propose compensating for the reduction in activity of the fixed catalyst bed substantially by increasing the temperature of the fixed catalyst bed gradually in the course of the operating time under otherwise substantially uniform operating conditions, in order to essentially retain the acrolein conversion in single pass of the reaction gas mixture through the fixed catalyst bed.

A disadvantage of the procedure recommended in EP-A 990636 and in EP-A 1106598 is that, with increasing raising of the temperature of the fixed catalyst bed, its aging process is accelerated increasingly (particular movement processes within the catalysts which contribute to aging proceed, for example, increasingly more rapidly). On attainment of a maximum value of the temperature of the fixed catalyst bed, the fixed catalyst bed finally has to be exchanged completely.

However, a disadvantage of such a complete exchange is that it is comparatively costly and inconvenient. The process for acrylic acid preparation has to be interrupted for a prolonged period and the costs of catalyst preparation are likewise considerable.

What are desired are therefore procedures which are helpful in prolonging the lifetime of the fixed catalyst bed in the reactor as far as possible.

In this regard, DE-A 10232748 recommends, instead of completely exchanging the fixed catalyst bed, replacing only a portion thereof by a fresh catalyst charge. A disadvantage of this procedure is that even a partial catalyst bed change is already comparatively costly and inconvenient and entails an interruption in the partial oxidation of acrolein to acrylic acid.

DE-A 102004025445 proposes, as a process for long-term operation of the heterogeneously catalyzed partial gas phase oxidation of acrolein to acrylic acid, counteracting the deactivation of the fixed catalyst bed by increasingly raising the working pressure in the gas phase with increasing operating time of the fixed catalyst bed. A disadvantage of this procedure is that, with increasing working pressure, increased compression outputs are required in the heterogeneously catalyzed partial gas phase oxidation.

EP-A 614872 recommends prolonging the lifetime of the fixed catalyst bed by, after an operating time of the fixed catalyst bed of several years, which is accompanied by increases in the temperature thereof of from 15° C. to 30° C. and more, interrupting the process for partial oxidation, and, at elevated temperature of the fixed catalyst bed, conducting a regeneration gas mixture composed of oxygen, steam and inert gas through it and then continuing the partial oxidation (in this connection, inert gases in a gas mixture which is conducted through a fixed catalyst bed under particular conditions shall be understood in this document quite generally to mean those gases which, in the course of conduct of the gas mixture through the fixed catalyst bed, remain unchanged to an extent of at least 95 mol %, preferably to an extent of at least 98 mol %, most preferably to an extent of at least 99 mol % or 99.5 mol %).

However, a disadvantage of the procedure of EP-A 614872 is that, up to the time of interruption, the aging of the fixed catalyst bed continues and is promoted uninhibited.

DE-A 10350822 attempts to remedy the disadvantage of EP-A 614872 by increasing the temperature of the fixed catalyst bed over the operating time to balance out the deactivation of the fixed catalyst bed, but interrupting the partial oxidation before this temperature increase is 8° C. and conducting an oxygen-comprising gas through the fixed catalyst bed in a regenerating manner. However, a disadvantage of the procedure of DE-A 10350822 is that each regeneration necessitates an interruption of the actual partial oxidation process.

A disadvantage of all prior art processes acknowledged above for prolonging the lifetime of a fixed catalyst bed suitable for performing a heterogeneously catalyzed partial oxidation of acrolein to acrylic acid is additionally that none of them attempt to counteract the occurrence of deactivation of the fixed catalyst bed in a preventative manner beforehand, but rather only commence when such a deactivation of the fixed catalyst bed has already occurred, in order to counteract the negative consequence of such a deactivation.

It was therefore an object of the present invention to provide a process which is suitable for preventatively counteracting a deactivation of coated catalysts whose active composition is a finely divided multielement oxide which comprises Mo and V and is applied to a support body in the course of a heterogeneously catalyzed partial gas phase oxidation of acrolein to acrylic acid (i.e. of delaying the onset of deactivation).

The object is achieved by a process for preparing a catalyst consisting of a support body and a catalytically active composition applied on the surface of the support body, in which the active composition is attached to the surface of the support body with the aid of a binder, wherein the active composition is a finely divided mixture of at least one finely divided multielement oxide comprising the elements Mo and V and at least one finely divided substance S selected from the group consisting of oxides of molybdenum and of compounds of molybdenum from which an oxide of molybdenum is formed under the action of elevated temperature and molecular oxygen.

An advantage of the inventive procedure is that the finely divided multielement oxide comprising Mo and V is prepared separately before the coating of the support body with the catalytically active composition. This has the consequence that its catalytic activity, with regard to the partial oxidation of acrolein to acrylic acid, is essentially not impaired by the addition of the finely divided substance S.

When the finely divided substance S is not already an oxide of molybdenum, it is possible alternatively in accordance with the invention to use a compound of molybdenum from which an oxide of molybdenum is formed under the action of elevated temperature and molecular oxygen. The elevated temperature and the molecular oxygen can, for example, act on the surface of the support body after the application of the finely divided active mixture to the surface of the support body. Appropriately from an application point of view, the temperature employed will be selected so as to be below the highest temperature employed to prepare the multielement oxide comprising Mo and V. To provide the molecular oxygen, the thermal treatment can be effected, for example, under molecular oxygen or under a mixture of molecular oxygen and inert gas (e.g. air).

Examples of finely divided substances S other than an oxide of molybdenum which are suitable in accordance with the invention include ammonium molybdate [$(NH_4)_2MoO_4$] and the ammonium polymolybdates, such as ammonium heptamolybdate tetrahydrate [$(NH_4)_6Mo_7O_{24} \cdot 4H_2O$]. An alternative example is molybdenum oxide hydrate ($MoO_3 \cdot xH_2O$). However, it is also possible to use molybdenum hydroxides as such substances S.

However, the elevated temperature and the molecular oxygen can also act on the substance S other than a molybdenum oxide actually through the heterogeneously catalyzed partial oxidation of acrolein to acrylic acid itself. In this case, the molybdenum oxide is formed actually during the performance of the heterogeneously catalyzed partial oxidation of acrolein to acrylic acid using coated catalysts prepared in accordance with the invention.

However, preference will be given in accordance with the invention to using, as the finely divided substance S, an oxide (e.g. $MoO_2$) of molybdenum (in this document, this is understood to mean a substance which consists only of Mo and O to an extent of $\geq 98\%$ by weight, preferably to an extent of $\geq 99\%$ by weight and more preferably to an extent of $\geq 99.9\%$ by weight). In the process according to the invention, the finely divided substance S used is more preferably molybdenum trioxide ($MoO_3$).

In principle, useful finely divided substances S are also molybdenum oxides such as $Mo_{18}O_{52}$, $Mo_8O_{23}$ and $Mo_4O_{11}$ (cf., for example, "Synthese und strukturelle Untersuchungen von Molybdän-, Vanadium-und Wolframoxiden als Referenzverbindungen für die heterogene Katalyse" [Synthesis and structural investigations of molybdenum oxides, vanadium oxides and tungsten oxides as reference compounds for heterogeneous catalysis], thesis by Dr. Andreas Blume, Faculty II Mathematics and Natural Sciences of the Technical University of Berlin, 2004, or Surface Science 292 (1993) 261-6, or J. Solid State Chem. 124 (1996) 104).

Appropriately from an application point of view, the specific surface area $O_M$ of a molybdenum oxide used advantageously as the finely divided substance S in the process according to the invention is, preferably in accordance with the invention, $\leq 10$ m$^2$/g, more preferably $\leq 5$ m$^2$/g and most preferably $\leq 2$ m$^2$/g. In general, the specific surface area $O_M$ will, however, be $\geq 0.01$ m$^2$/g, frequently $\geq 0.05$ m$^2$/g and in many cases $\geq 0.1$ m$^2$/g.

The specific surface area is understood to mean the BET surface area (determined by gas adsorption ($N_2$) according to Brunauer-Emmett-Teller (BET)). The above statements regarding $O_M$ apply especially when the finely divided molybdenum oxide is $MoO_3$. The reason for the advantageousness of a low value for $O_M$ is that a molybdenum oxide with a low value for $O_M$ behaves substantially inertly in the course of a heterogeneously catalyzed partial gas phase oxidation of acrolein to acrylic acid. In other words, particularly advantageously in accordance with the invention, the finely divided substance S used will be such molybdenum oxide (especially $MoO_3$) that, when the coated catalyst (same support body, same coating thickness, same particle size of the finely divided composition applied to the support) is prepared using solely molybdenum oxide (especially $MoO_3$) as the "active composition" under the conditions under which, in the case of use of a coated catalyst which has been prepared using solely the finely divided multielement oxide comprising the elements Mo and V as the active composition, an acrolein conversion of from 95 to 100 mol % (based on single pass of the reaction gas mixture through the fixed catalyst bed charged otherwise identically with the particular coated catalyst) is achieved, only an acrolein conversion of $\leq 10$ mol %, preferably of $\leq 5$ mol % and very particularly of $\leq 2$ mol % or of $\leq 1$ mol % is achieved.

The granularity (particle diameter and particle diameter distribution) of the finely divided substance S is, advantageously in accordance with the invention, identical to that of the finely divided multielement oxide comprising the elements Mo and V (this enables particularly homogeneous mixing with the finely divided multielement oxide). This is especially true when the finely divided substance S is a molybdenum oxide (especially $MoO_3$).

However, it will be appreciated that the granularity of the finely divided substance S in processes according to the invention may also be different from that of the finely divided multielement oxide comprising the elements Mo and V.

Particle diameter distributions and particle diameters $d_x$ taken therefrom (for example $d_{10}$, or $d_{50}$, or $d_{90}$) are based on determinations to ISO 13320 with the Malvern Mastersizer S laser diffraction spectrometer (Malvern Instruments, Worcestershire WR14 1AT, United Kingdom). The particle diameters $d_x$ reported as the measurement result are defined such that X % of the total particle volume consists of particles having this or a smaller diameter.

To determine particle diameter distributions, the particular finely divided powder is, appropriately from an application point of view, conducted through a dispersing channel into the Sympatec RODOS dry disperser (Sympatec GmbH, System-Partikel-Technik, Am Pulverhaus 1, D-38678 Clausthal-Zellerfeld) and dry-dispersed there with compressed air and blown into the measurement cell in a free jet. The actual laser diffraction determination is then effected therein.

Quite generally, the granularity of the finely divided substance S to be used in accordance with the invention (especially when it is a molybdenum oxide (e.g. $MoO_3$)) in the process according to the invention should be such that the longest dimension $d_L$ (longest direct line connecting two points on the particle surface) of $\geq 50\%$, preferably of $\geq 75\%$, of the total volume of all particles is $\leq 800$ μm, advantageously $\leq 600$ μm, more advantageously $\leq 400$ μm or $\leq 300$ μm and most advantageously $\leq 200$ μm or $\leq 100$ μm.

In general, the granularity of the finely divided substance S to be used in accordance with the invention (especially when it is a molybdenum oxide (e.g. $MoO_3$) in processes according to the invention should be such that $d_L$ of $\geq 50\%$, preferably of $\geq 75\%$, of the total volume of all particles is $\geq 0.1$ μm, frequently $\geq 0.5$ μm and in many cases $\geq 1$ μm.

In other words, useful finely divided substances S (especially molybdenum oxides (e.g. $MoO_3$)) for the process according to the invention are especially those for which 0.1 μm$\leq d_{50} \leq 800$ μm, advantageously 0.5 μm$\leq d_{50} \leq 600$ μm, preferably 0.75 μm$\leq d_{50} \leq 400$ μm (or $\leq 300$ μm), more preferably 1 μm$\leq d_{50} \leq 200$ μm (or $\leq 100$ μm).

In principle, in the process according to the invention, the granularity of the finely divided substance S (especially in the case of a molybdenum oxide (e.g. $MoO_3$) is adjusted to the desired thickness $D_A$ of the active composition coating on the surface of the support body.

In other words, in general, $d_{50}$ will be $\leq D_A$, preferably $\leq 0.75 \cdot D_A$, more preferably $\leq 0.5 \cdot D_A$ and most preferably $\leq 0.3 \cdot D_A$.

Normally, $d_{50}$ will, however, be $\geq 0.001 \cdot D_A$, or $\geq 0.01 \cdot D_A$, frequently $\geq 0.05 \cdot D_A$ and in many cases $\geq 0.1 \cdot D_A$.

The total use amount of finely divided substance S will, based on the total use amount of finely divided multielement oxide comprising Mo and V, in the process according to the invention, appropriately from an application point of view, be >0 and $\leq 50\%$ by weight. Advantageously in accordance with the invention, the aforementioned use amount on the same basis will be $\geq 0.1$, usually $\geq 0.5$ and frequently $\geq 1\%$ by weight. In many cases, the aforementioned use amount on the same basis will be $\leq 40\%$ by weight or $\leq 30\%$ by weight. Preferably in accordance with the invention, the aforementioned use amount on the same basis will be $\geq 5$ and $\leq 20\%$ by weight (or $\leq 15\%$ by weight). The aforementioned quantitative data are especially true when the finely divided substance S is a molybdenum oxide (e.g. $MoO_3$).

In principle, a molybdenum oxide (e.g. $MoO_3$) suitable as the finely divided substance S for the process according to the invention may be obtained in a controlled manner from another substance comprising Mo.

For this purpose, it is possible to proceed, for example, from ammonium heptamolybdate tetrahydrate $[(NH_4)_6Mo_7O_{24} \cdot 4H_2O]$. For example, thermal treatment at 350° C. for 3 hours in an airstream likewise having a temperature of 350° C. converts it to $MoO_3$. The granularity of the $MoO_3$ can be adjusted as required by appropriate grinding and screening. In a corresponding manner, it is also possible to adjust the specific surface area of the $MoO_3$ as desired. With increasing duration of the thermal treatment and/or increase in the temperature of the thermal treatment (on completion of $MoO_3$ formation under inert gas or under molecular oxygen-comprising gas atmosphere (e.g. air)), the specific surface area decreases.

On completion of formation of the $MoO_3$ at 350° C., thermal treatment at from 550 to 650° C. for from 4 to 8 hours in an airstream having an appropriate temperature is generally sufficient to suppress the specific surface area $O_M$ of the $MoO_3$ to a value of $\leq 2$ m$^2$/g.

However, it will be appreciated that molybdenum oxides suitable as the finely divided substance S for the process according to the invention may also be purchased commercially.

DESCRIPTION OF THE DRAWINGS

An example of molybdenum oxide suitable for the process according to the invention is $MoO_3$ from Climax Molybdenum Marketing Corporation (Phoenix, USA) which has an Mo content of 66.60% by weight and a specific surface area $O_M$ of 3.7 m$^2$/g (trade name: "pure Moly Oxide Crystalline POC"). FIG. 1 shows the particle diameter distribution determined for this $MoO_3$ to ISO 13320 (laser, Malvern). In this figure, the abscissa shows the diameters [μm] on a logarithmic scale. The ordinate shows the volume fraction of the $MoO_3$ which has the particular diameter or a smaller diameter. The commercially available product has the particle diameter distribution X shown in FIG. 1. However, these particles are agglomerates of primary particles. The action of, for example, ultrasound can bring about the decomposition of the agglomerates to the primary particles. These have the particle diameter distribution O shown in FIG. 1. Useful particle diameter distributions for the process according to the invention are all of those which can be obtained by blending the particle diameter distributions X and O shown in FIG. 1 (in any quantitative ratios (for example from 1000:1 to 1:1000, or from 100:1 to 1:100, or from 10:1 to 1:10, or from 5:1 to 1:5, or from 2:1 to 1:2)). In practice, these particle diameter distributions can be obtained, for example, by mixing primary particles and agglomerate with one another in the appropriate quantitative (weight) ratio.

In general, the aforementioned $MoO_3$ additionally has the following extraneous constituent specification:

Na $\leq 8$ ppm by weight,
K $\leq 29$ ppm by weight,
Fe $\leq 4$ ppm by weight,
Pb $\leq 1$ ppm by weight,
Al $\leq 4$ ppm by weight,
Cr $\leq 2$ ppm by weight,
Ca $\leq 2$ ppm by weight,
Cu $\leq 2$ ppm by weight,
Mg $\leq 5$ ppm by weight,
Ni $\leq 2$ ppm by weight,
Si $\leq 5$ ppm by weight,
Sn $\leq 1$ ppm by weight, and
Ti $\leq 2$ ppm by weight.

However, it will be appreciated that it is also possible in accordance with the invention to use $MoO_3$ from the Climax Molybdenum Marketing Corporation of the commercial type "POS".

Alternatively, the commercially available $MoO_3$ used for the process according to the invention may also be $MoO_3$ from H.C. Starck, D-38615 Goslar (trade name: "Molybdenum Trioxide I").

This has a specific surface area $O_M$ of 1 m$^2$/g. The Mo content of this $MoO_3$ is 66.6% by weight.

Otherwise, this $MoO_3$ suitable in accordance with the invention from H. C. Starck has the following extraneous component specification:

$NH_4 \leq 0.01\%$ by weight,
Al $\leq 10$ ppm by weight,
Ca $\leq 5$ ppm by weight,
Co $\leq 10$ ppm by weight,
Cr $\leq 5$ ppm by weight,
Cu $\leq 5$ ppm by weight,
Fe $\leq 10$ ppm by weight,
K $\leq 80$ ppm by weight,
Mg $\leq 5$ ppm by weight,
Mn $\leq 10$ ppm by weight,
Na $\leq 20$ ppm by weight,
Ni $\leq 5$ ppm by weight,
P $\leq 10$ ppm by weight,
Pb $\leq 10$ ppm by weight,
Si $\leq 10$ ppm by weight,
Sn $\leq 10$ ppm by weight,
Ti $\leq 5$ ppm by weight,
V $\leq 10$ ppm by weight,
Zn $\leq 10$ ppm by weight, and
Zr $\leq 10$ ppm by weight.

Figure 2:
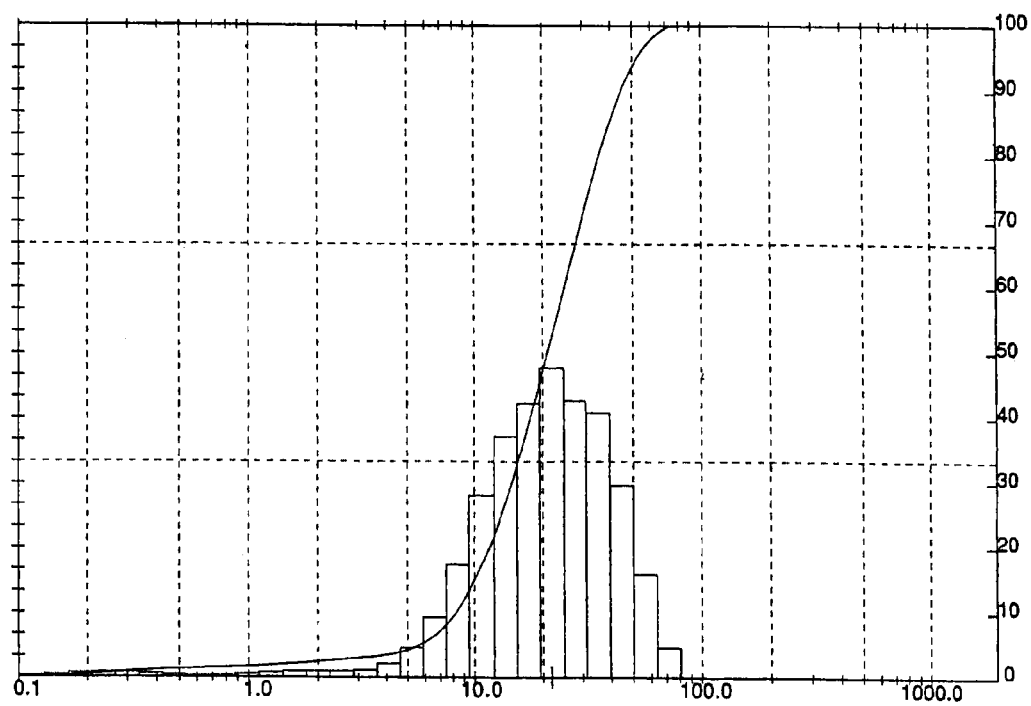
FIG. 2: Particle diameter distribution (volume fraction versus diameters (μm) on a logarithmic scale) determined for MoO3 from H.C. Starck.

The accompanying particle diameter distribution is shown by FIG. 2. In this figure, the abscissa shows the diameters [μm] on a logarithmic scale. The ordinate shows the volume fraction of the $MoO_3$ which has the particular diameter or a smaller diameter.

The $MoO_3$ particles of the $MoO_3$ from H. C. Starck are likewise agglomerates of primary particles. Unlike the $MoO_3$ particles of the $MoO_3$ from Climax, the primary particles are, however, highly cohesive, which is why the action of, for example, ultrasound cannot bring about decomposition to the primary particles.

It will be appreciated that it is also possible in accordance with the invention to use molybdenum trioxides of the "II" types from H.C. Starck.

Otherwise, it is also possible to use $MoO_3$ from the following manufacturers for the process according to the invention:

Metal-Tech.-Ltd. (Israel), purity >98% by weight, $O_M=1.1$ m²/g;
Gulf Chemical (Texas, USA), 65.76% by weight Mo, $O_M=1.2$ m²/g;
Nanjing Chemical Industries (China), 66.6% by weight Mo, $O_M=0.8$ m²/g;
Kankal Exports (India), purity $\geq 99\%$ by weight, $O_M=1.7$ m²/g;
Taiyo Koko Co., Ltd. (Japan), purity $\geq 99.7\%$ by weight, $O_M=1.6$ m²/g;
Anhui Chizhou Huangshanling Lead and Zinc Mine (China), purity $\geq 99.7\%$ by weight, 66.5% by weight Mo, $O_M=0.3$ m²/g;
CCl Moly B.V. (The Netherlands), purity >99.5% by weight, >66% by weight Mo, $O_M=2.5$ m²/g.

Useful finely divided multielement oxides comprising the elements Mo and V include all multielement oxide compositions known in the prior art which are capable of catalyzing the partial oxidation of acrolein to acrylic acid.

These are in particular the multielement oxide compositions comprising Mo and V of DE-A 102005010645, WO 95/11081, DE-A 10350822, US-A 2006/0205978, EP-A 714700, DE-A 102004025445, WO 2004/108267, WO 2004/108284 and all documents cited in the aforementioned prior art documents. Particularly preferred multielement oxides comprising Mo and V for the process according to the invention are the exemplary embodiments (especially Working Example 1) of WO 2004/108267. It is also possible to employ all preparation processes disclosed in these documents for the preparation of multielement oxide compositions comprising Mo and V which are suitable in accordance with the invention. It is equally possible to use the coated catalysts obtainable in accordance with the invention to configure the fixed catalyst bed in all processes for heterogeneously catalyzed partial gas phase oxidation of acrolein to acrylic acid disclosed in the aforementioned documents. Useful support bodies for the process according to the invention are in principle all support bodies recommended in the aforementioned documents.

The molar proportion of the element Mo in the total amount of all elements other than oxygen in the finely divided multielement oxides comprising Mo and V which are suitable in accordance with the invention is generally from 5 to 95 mol %, frequently from 10 to 90 mol % and in many cases from 15 to 85 mol % or from 20 to 80 mol %. The molar ratio of Mo to V in the finely divided multielement oxide compositions comprising Mo and V which are suitable for the process according to the invention is generally from 15:1 to 1:1, frequently from 12:1 to 2:1.

In addition to Mo, V and O, finely divided multielement oxides suitable in accordance with the invention frequently also comprise at least one of the elements Nb and W. In many cases, the molar ratio of Mo/(total amount of W and Nb) in such multielement oxides is from 80:1 to 1:4. Frequently, such multielement oxide compositions suitable in accordance with the invention also comprise Cu in the appropriate molar Mo/Cu ratio of from 30:1 to 1:3. In addition to the elements Nb and/or W and also Mo, V, O and if appropriate Cu, finely divided multielement oxides suitable for the process according to the invention may additionally comprise, for example, at least one of the elements Ta, Cr, Ce, Ni, Co, Fe, Mn, Zn, Sb, Bi, alkali metal (Li, Na, K, Rb, Cs), H, alkaline earth metal (Mg, Ca, Sr, Ba), Si, Al, Ti and Zr. Of course, the finely divided multielement oxide composition to be used in accordance with the invention may also consist only of the elements Nb and/or W, or else Mo, V, O and if appropriate Cu.

Finely divided multielement oxides comprising Mo and V to be used in accordance with the invention are in principle obtainable by preparing, from starting compounds which comprise the elemental constituents of the multielement oxide composition other than oxygen as constituents, an intimate dry mixture (also known as precursor composition) and thermally treating (calcining) it at temperatures of from 200 to 600° C., preferably from 300 to 450° C. (material temperature). Preference is given to effecting the thermal treatment in a gas atmosphere comprising $O_2$ and $NH_3$. The $NH_3$ may evolve from the precursor composition itself by virtue of an appropriate amount of ammonium ions being incorporated into it. More preferably (cf. EP-A 72448, WO 2004/108267 and WO 95/11081), the thermal treatment is effected such that the gas atmosphere in which the thermal treatment is effected comprises at all times from 0.5 to 4% by volume of $O_2$, averaged over the overall duration of the thermal treatment, from 1 to 8% by volume of $NH_3$, and steam and/or inert gas as the remainder, where the $NH_3$ content of the atmosphere passes through a maximum which is below 20% by volume during the thermal treatment.

Some multielement oxide compositions comprising Mo and V which are favorable in accordance with the invention satisfy the following general stoichiometry I

 (I)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40 and
n=a number which is determined by the valency and frequency of the elements in I other than oxygen.

Among the finely divided multielement oxide compositions (I) suitable in accordance with the invention, preference is given in turn to those in which the variables are within the following ranges:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=2.5 to 5,
b=0.5 to 2,
c=0.5 to 3,
d=0 to 2,
e=0 to 0.2,
f=0 to 1,
g=0 to 15 and
n=a number which is determined by the valency and frequency of the elements in I other than oxygen.

Very particularly preferred multielement oxide active compositions suitable in accordance with the invention satisfy the general stoichiometry II

 (II)

in which the variables are each defined as follows:
$X^1$=W and/or Nb,
$X^2$=Cu and/or Ni,
$X^5$=Co and/or Sr,
$X^6$=Si and/or Al,
a=3 to 4.5,
b=1 to 1.5,
c=0.75 to 2.5,
f=0 to 0.5,
g=0 to 8 and
n=a number which is determined by the valency and frequency of the elements in II other than oxygen.

For the preparation of such finely divided multielement oxide compositions and other finely divided multielement oxide compositions suitable in accordance with the invention, the starting materials are, as already stated, in a manner known per se, suitable sources (starting compounds) of the elemental constituents of the desired multielement oxide composition other than oxygen in the particular stoichiometric ratio desired in the multielement oxide composition, and a very intimate, preferably finely divided, dry mixture is obtained therefrom and is then subjected to the thermal treatment. The sources may already either be oxides or be compounds which can be converted to oxides by heating, at least in the presence of oxygen. In addition to the oxides, useful starting compounds are therefore in particular halides, nitrates, formates, oxalates, acetates, carbonates or hydroxides.

Suitable starting compounds of Mo, V, W and Nb are also their oxo compounds (molybdates, vanadates, tungstates and niobates) and the acids derived therefrom. Oxygen-containing sources are likewise favorable.

A content in the intimate dry mixture of ammonium ions, which is advantageous as described above, can be realized in a simple manner by incorporating an appropriate amount of ammonium ions into the intimate dry mixture. Appropriately, the ammonium ions can be introduced into the intimate dry mixture by, for example, using the corresponding ammonium oxometalates as sources of the elements Mo, V, W or Nb. Examples thereof are ammonium metaniobate, ammonium metavanadate, ammonium heptamolybdate tetrahydrate and ammonium paratungstate heptahydrate. It will be appreciated that it is also possible to incorporate ammonium suppliers such as $NH_4NO_3$, or $NH_4Cl$, or ammonium acetate, or ammonium carbonate, or ammonium hydrogencarbonate, or $NH_4OH$, or $NH_4CHO_2$, or ammonium oxalate, into the intimate dry mixture to be treated thermally irrespective of the starting compounds required as sources of the multielement oxide composition constituents.

The intimate mixing of the starting compounds can in principle be effected in dry or in wet form.

Preference is given to effecting the intimate mixing in wet form. Typically, the starting compounds are mixed with one another in the form of an aqueous solution and/or suspension. Particularly intimate dry mixtures are obtained in the mixing process described when the starting materials used are exclusively sources and starting compounds present in dissolved form. The solvent used is preferably water. Subsequently, the aqueous composition (solution or suspension) is dried and the intimate dry mixture thus obtained is, if appropriate, immediately treated thermally. Preference is given to effecting the drying process by spray-drying (the exit temperatures are generally from 100 to 150° C.) and immediately after the completion of the aqueous solution or suspension. The powder obtained is frequently found to be too finely divided for immediate further use, which is why it is then appropriately kneaded with addition of, for example, water. In many cases, an addition of a lower organic carboxylic acid (e.g. acetic acid) is found to be advantageous for the kneading (typical added amounts are from 5 to 10% by weight based on the powder composition used).

The kneaded material obtained is then, appropriately from an application point of view, shaped to extrudates, these are treated thermally as already described and then ground to a finely divided powder which can be used in the process according to the invention as such or concentrated to a desired particle size.

Support materials suitable for coated catalysts obtainable in accordance with the invention are, for example, porous or nonporous (preferred) aluminum oxides, silicon dioxide, thorium dioxide, zirconium dioxide, silicon carbide or silicates such as magnesium silicate or aluminum silicate (for example C 220 steatite from CeramTec). The materials of the support bodies are preferably chemically inert, i.e. they essentially do not intervene in the course of the gas phase partial oxidation which is catalyzed by the coated catalysts prepared in accordance with the invention.

The support bodies may be of regular or irregular shape, preference being given to regularly shaped support bodies with marked surface roughness, for example spheres, cylinders or hollow cylinders with a grit layer. Their longest dimension is generally from 1 to 10 mm.

The support materials may be porous or nonporous. The support material is preferably nonporous (total volume of the pores based on the volume of the support body advantageously ≦1% by volume).

An increased surface roughness of the support body generally causes an increased adhesion strength of the applied coating of finely divided active composition.

The surface roughness $R_Z$ of the support body is preferably in the range from 30 to 100 μm, preferably from 50 to 70 μm (determined to DIN 4768 sheet 1 with a "Hommel Tester for DIN-ISO surface area parameters" from Hommelwerke). Particular preference is given to surface-rough support bodies from CeramTec composed of steatite C 220.

It is particularly suitable in accordance with the invention to use essentially nonporous, surface-rough, spherical supports composed of steatite (for example C 220 steatite from CeramTec), whose diameter is from 1 to 8 mm, preferably from 4 to 5 mm. It is also suitable to use cylinders as support bodies, whose length is from 2 to 10 mm and whose external diameter is from 4 to 10 mm. In the case of rings as support bodies, the wall thickness is additionally typically from 1 to 4 mm. Annular support bodies to be used with preference have a length of from 2 to 6 mm, an external diameter of from 4 to 8 mm and a wall thickness of from 1 to 2 mm. In particular, suitable support bodies are also rings of geometry 7 mm×3 mm×4 mm (external diameter×length×internal diameter).

The finely divided mixture of at least one finely divided multielement oxide comprising the elements Mo and V and at least one finely divided substance S to be applied in accordance with the invention to the surface of the support body should be a very homogeneous mixture. In order to prepare such a homogeneous mixture from the finely divided starting materials, it is possible, for example, to use an R 645 mixer from AMK in Aachen (Germany). This is an inclined mixer with cutting lobes (intensive mixer). The mixing arm rotates, for example, at 39 revolutions per minute and the cutting lobe at 3000 revolutions per minute. It will be appreciated that it is also possible to use other mixers. For example, it is also possible to use an Eirich intensive mixer (model R 02) from Maschinenfabrik Gustav Eirich GmbH & Co. KG, D-74736 Hardheim.

The (coating) thickness $D_A$ of the active composition applied to the support body in the process according to the invention is generally appropriately from 10 to 1000 μm. Especially in the case of annular support bodies, from 10 to 500 μm are preferred, from 100 to 500 μm more preferred and from 200 to 300 or from 150 to 250 μm most preferred.

The granularity (fineness) of the finely divided multielement oxide comprising Mo and V is of course, in the same way as the granularity of the finely divided substance S, appropriately from an application point of view, adjusted to the desired coating thickness $D_A$. All statements made with regard to the longest dimension $d_L$ of the finely divided substance S therefore apply correspondingly to the longest dimension $d_L$ of the finely divided multielement oxide comprising Mo and V.

For the preferred range of a coating thickness $D_A$ of from 100 to 500 μm, suitable multielement oxides are in particular those finely divided multielement oxides comprising Mo and V of which ≧50%, preferably ≧75%, of the total volume of all particles passes through a sieve of mesh size from 1 to 20 μm, preferably from 1 to 10 μm, and whose fraction of particles having a longest dimension $d_L$ of above 50 μm and below 0.2 μm is less than 1% of the total volume of all particles. In general, the distribution of the longest dimension $d_L$, both of the finely divided substance S and of the finely divided multielement oxide comprising Mo and V, as a result of the preparation, corresponds to a Gaussian distribution. Most preferably in accordance with the invention, the finely divided multielement oxide comprising Mo and V, for the coating thickness $D_A$ range of from 100 to 500 μm, has the particle diameter distribution shown in FIG. 3. The abscissa shows the diameters [μm] on a logarithmic scale. The ordinate shows the volume fraction which has the particular diameter or a smaller diameter.

The attachment (application) of the finely divided active composition to the surface of the support body can be effected in the process according to the invention in accordance with the processes described for this purpose in the prior art (cf., for example, US-A 2006/0205978 and EP-A 714700, and the prior art cited in these two documents).

Appropriately in accordance with the invention, the application of the active composition to the surface of the support body will be undertaken with the aid of a liquid binder. Useful such liquid binders include, for example, water, an organic solvent or a solution of an organic substance (for example of an organic solvent) in water or in an organic solvent.

Examples of organic binders include mono- or polyhydric organic alcohols, for example ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, and mono- or polyfunctional organic amides such as formamide. Suitable organic binder promoters soluble in water, in an organic liquid or in a mixture of water and an organic liquid are, for example, monosaccharides and oligosaccharides such as glucose, fructose, sucrose and/or lactose.

Particularly advantageously, the liquid binder used is a solution consisting of from 20 to 90% by weight of water and from 10 to 80% by weight of an organic compound. The organic proportion in the aforementioned liquid binders is preferably from 10 to 50% by weight and more preferably from 20 to 30% by weight.

Preference is generally given to those organic binders or binder fractions whose boiling point or sublimation temperature at standard pressure (1 atm) is ≧100° C., preferably ≧150° C. Most preferably, the boiling point or sublimation point of such organic binders or binder fractions at standard pressure is simultaneously below the highest (calcination) temperature employed in the course of the preparation of the finely divided multielement oxide comprising the elements Mo and V. Typically, this highest calcination temperature is ≦600° C., frequently ≦500° C. or ≦400° C., in many cases even ≦300° C. Particularly preferred liquid binders are solutions which consist of from 20 to 90% by weight of water and from 10 to 80% by weight of glycerol. The glycerol content in these aqueous solutions is preferably from 10 to 50% by weight and more preferably from 20 to 30% by weight. One reason for the advantageousness of binders preferred in accordance with the invention is that they are capable of wetting both the finely divided active composition and the support bodies completely satisfactorily.

The application (attachment) of the finely divided mixture composed of at least one finely divided multielement oxide comprising the elements Mo and V and at least one finely divided substance S can be effected in a particularly simple manner by dispersing the finely divided mixture in the liquid binder and spraying the resulting suspension onto moving and, if appropriate, hot support bodies (cf., for example, DE-A 1642921, DE-A 2106796 and DE-A 2626887).

After the spray application has ended, following the teaching of DE-A 2909670, the moisture content of the resulting coated catalysts can be reduced by passing over hot air. With regard to the residual moisture remaining in a coated catalyst prepared in accordance with the invention, appropriately from an application point of view, the teaching of DE-A 102005010645 will be followed.

Preferably in accordance with the invention, the attachment of the finely divided active composition to the support body surface in the process according to the invention will, however, be undertaken (cf. DE-A 2526238, U.S. Pat. No. 3,956,377, DE-A 235151, DE-A 2909671 and EP-A 714700) in such a way that the support bodies are first moistened with the liquid binder and then finely divided active composition is attached to the binder-moistened support material (applied to its surface) by rolling the moistened support material in the finely divided active composition.

To achieve the desired coating thickness, the above-described process is advantageously repeated periodically. In other words, the base-coated support body then forms the support body which, in the next period, is to be first moistened and then coated by contact with dry finely divided active composition.

For performance of the process according to the invention on the industrial scale, it is therefore advisable advantageously to employ the process principle disclosed in DE-A 2909671, except preferably using the binder recommended in EP-A 714700.

In other words, the support bodies to be coated are charged into a preferably inclined (the angle of inclination is generally from 30 to 90°) rotating vessel (for example rotary pan or coating drum). The rotating vessel conducts the especially spherical or cylindrical, in particular hollow cylindrical, support bodies under two metering devices arranged in succession at a particular distance. The first of the two metering devices corresponds appropriately to a nozzle by which the support bodies rolling in the rotating pan are sprayed with the liquid binder to be used and moistened in a controlled manner. The second metering device is outside the atomization cone of the sprayed liquid binder and serves to supply the finely divided active composition (for example via an agitated channel). The support spheres moistened in a controlled manner take up the active composition powder supplied, which is compacted by the rolling motion on the outer surface of the cylindrical or spherical support bodies to form a coherent coating (such a compacting motion does not take place in the inner circle of a hollow cylindrical support body, which is why it remains essentially uncoated).

If required, the support body thus base-coated, in the course of the next rotation, again passes through the spray nozzle, is moistened in a controlled manner as it does so in order to be able to take up a further layer of finely divided oxidic active composition in the course of further movement, etc. (intermediate drying is generally not required). The liquid binder used in accordance with the invention can, following the teaching of DE-A 102005010645, be removed partly or completely, for example, by final heat supply, for example by the action of hot gases such as $N_2$ or air. A particular advantage of the above-described embodiment of the process according to the invention consists in being able to prepare coated catalysts with coatings consisting of two or more different active compositions in coating form in one working step. Remarkably, the process according to the invention brings about both completely satisfactory adhesion of the successive layers to one another and of the base layer on the surface of the support body. This is also true in the case of annular support bodies.

It is essential for the above-described embodiment of the process according to the invention that the moistening of the surface of the support body to be coated is undertaken in a controlled manner. In short, this means that the support surface is appropriately moistened in such a way that it does have adsorbed liquid binder but no liquid phase as such is visually apparent on the support surface. When the support body surface is too moist, the finely divided active composition agglomerates to form separate agglomerates, instead of attaching to the surface. More detailed information on this subject can be found in DE-A 2909671.

One advantage of the above-described process consists in the fact that the removal of the liquid binder used can be undertaken in a controlled manner, for example by evaporation and/or sublimation. In the simplest case, this can be effected by the action of hot gases of appropriate temperature (for example from 50 to 200° C., frequently from 100 to 150° C.). However, the action of hot gases, following the teaching of DE-A 102005010645, can also bring about only partial drying. The final drying can then be effected, for example, in the reactor for the relevant partial oxidation itself (of course, subsequent drying up to full drying could also be effected in a drying oven of any kind (for example in a belt dryer)). In principle, the temperature acting in the course of drying, advantageously in accordance with the invention, should not be above the calcination temperature employed to prepare the finely divided multielement oxide composition comprising the elements Mo and V.

At this point, it should be emphasized that finely divided multielement oxide compositions suitable for the process according to the invention are also those which comprise, as elements other than oxygen, at least one of the two elements Te and Sb as well as the elements Mo and V, and at least one of the elements from the group comprising Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination.

Their preparation can be effected, for example, as described on pages 25, 26 of WO 2004/108267.

From the latter group of elements, the combination preferably comprises the elements Nb, Ta, W and/or Ti and more preferably the element Nb.

The aforementioned finely divided multielement oxide compositions preferably comprise the aforementioned element combination in the stoichiometry III $$Mo_1V_bM^1_cM^1_cM^2_d \qquad (III),$$

where
$M^1$=Te and/or Sb,
$M^2$=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=0.01 to 1,
c=>0 to 1, and
d=>0 to 1.

Preferably, $M^1$=Te and $M^2$=Nb, Ta, W and/or Ti. Preferably, $M^2$=Nb.

The stoichiometric coefficient b is advantageously from 0.1 to 0.6. In a corresponding manner, the preferred range for the stoichiometric coefficient c is from 0.01 to 1 or from 0.05 to 0.4, and favorable values for d are from 0.01 to 1 or from 0.1 to 0.6.

It is particularly favorable when the stoichiometric coefficients b, c and d are simultaneously within the aforementioned preferred ranges.

The aforementioned is especially true when the active composition, with regard to its elements other than oxygen, consists of an aforementioned element combination.

In that case, these are in particular the multielement oxide active compositions of the general stoichiometry IV

$$Mo_1V_bM^1_cM^2_dO_n \quad (IV)$$

where the variables are each as defined for the stoichiometry III and n=a number which is determined by the valency and frequency of the elements in (IV) other than oxygen.

Also suitable for the process according to the invention are those multielement oxide compositions which firstly either comprise one of the aforementioned element combinations or, with regard to the elements other than oxygen, consist of them and simultaneously have an X-ray diffractogram which has reflections h and i whose peak locations are at the reflection angles (2Θ) of 22.2±0.5° (h) and 27.3±0.5° (i) (all data relating to an X-ray diffractogram in this document are based on an X-ray diffractogram generated using Cu-Kα radiation as the X-ray source (Theta-Theta D-5000 Siemens diffractometer, tube voltage: 40 kV, tube current: 40 mA, aperture V20 (variable), collimator V20 (variable), secondary monochromator aperture (0.1 mm), detector aperture (0.6 mm), measuring interval (2Θ): 0.02°, measuring time per step: 2.4 s, detector: scintillation counting tube)).

The half-height width of these reflections may be very small or else very marked.

Particularly suitable aforementioned multielement oxide compositions for the process according to the invention are those multielement oxide compositions whose X-ray diffractogram, in addition to the reflections h and i, has a reflection k whose peak location is at 28.2±0.5° (k).

Among the latter, for an inventive use, preference is given in turn to those in which the reflection h has the highest intensity within the X-ray diffractogram and has a half-height width of at most 0.5°, and the process according to the invention is most preferably suitable for those in which the half-height width of the reflection i and of the reflection k is simultaneously in each case ≦1°, and the intensity $P_k$ of the reflection k and the intensity $P_i$ of the reflection i satisfy the relationship 0.2≦R≦0.85, better 0.3≦R≦0.85, preferably 0.4≦R≦0.85, more preferably 0.65≦R≦0.85, even more preferably 0.67≦R≦0.75 and most preferably R=0.70 to 0.75 or R=0.72, in which R is the intensity ratio defined by the formula $$R=P_i/(P_i+P_k).$$

The aforementioned X-ray diffractograms preferably do not have a reflection whose maximum is at (2Θ)=50±0.3°.

In this document, the definition of the intensity of a reflection in the X-ray diffractogram is based on the definition laid down in DE-A 19835247, DE-A 10122027, and in DE-A 10051419 and DE-A 10046672. The same applies to the definition of the half-height width.

In addition to the reflections h, i and k, the aforementioned X-ray diffractograms of multielement oxide active compositions to be used advantageously in accordance with the invention comprise further reflections whose peak locations are at the following reflection angles (2Θ):
9.0±0.4° (l)
6.7±0.4° (O) and
7.9±0.4° (p).

It is also favorable when the X-ray diffractogram additionally comprises a reflection whose peak location is at the reflection angle (2Θ)=45.2±0.4° (q).

Frequently, the X-ray diffractogram also comprises the reflections 29.2±0.4° (m) and 35.4±0.4° (n).

It is also favorable when the element combinations defined in the formulae III and IV are present as a pure i phase. When the multielement oxide composition also comprises a k phase, its X-ray diffractogram comprises, as well as those mentioned above, further reflections whose peak locations are at the following reflection angles (2Θ): 36.2±0.4° (m) and 50±0.4° (the terms "i and k phase" are used in this document as laid down in DE-A 10122027 and DE-A 10119933).

If the intensity 100 is assigned to the reflection h, it is favorable when the reflections i, l, m, n, o, p, q on the same intensity scale have the following intensities:
i: 5 to 95, frequently 5 to 80, in some cases 10 to 60;
l: 1 to 30;
m: 1 to 40;
n: 1 to 40;
o: 1 to 30;
p: 1 to 30 and
q: 5 to 60.

When the X-ray diffractogram comprises additional reflections from those mentioned above, the half-height width thereof is generally ≦1°.

The specific surface area of multielement oxide compositions of the general formula IV to be used in accordance with the invention or of multielement oxide compositions which comprise element combinations of the general formula III is in many cases from 1 to 30 m²/g (BET surface area, nitrogen), in particular when their X-ray diffractogram is configured as described.

As already mentioned, the coated catalysts obtainable in accordance with the invention are suitable in particular for performing the heterogeneously catalyzed partial gas phase oxidation of acrolein to acrylic acid. They are notable in particular in that a fixed catalyst bed charged with them has an increased lifetime in the performance of the aforementioned partial oxidation.

This is true in particular when the heterogeneously catalyzed partial gas phase oxidation of acrolein to acrylic acid is performed at high acrolein loads, as described, for example, by DE-A 10307983, DE-A 19948523 and DE-A 19910508.

In general, the gas phase partial oxidation of acrolein is performed in a tube bundle reactor having one or more temperature zones, as described, for example, in EP-A 700714, EP-A 700 893, DE-A 19910508, DE-A 19948523, DE-A 19910506, DE-A 19948241, DE-C 2830765, DE-C 2513405, U.S. Pat. No. 3,147,084, DE-A 2201528, EP-A 383224 and DE-A 2903218.

The solid catalyst charge is disposed in the metal tubes (catalyst tubes) of the tube bundle reactor, and the heating medium/media is/are conducted around the metal tubes (in the case of more than one temperature zone, a corresponding number of spatially separate heating media are conducted around the metal tubes). The heating medium is generally a salt melt. The reaction mixture is conducted through the catalyst tubes.

The fixed bed catalyst charge may consist only of catalysts obtainable in accordance with the invention, but also of such catalysts diluted with inert shaped bodies. The inert shaped bodies used may, for example, be the shaped support bodies (support bodies) used to prepare inventive coated catalysts. Upstream of and/or beyond the fixed bed catalyst charge may be disposed a pure inert shaped body bed (such pure inert shaped body beds are normally not included in the calculation of the loading of the fixed catalyst bed with reaction gas or with a reaction gas component).

The catalyst tubes are typically manufactured from ferritic steel and typically have a wall thickness of from 1 to 3 mm. Their internal diameter is generally from 20 to 30 mm, frequently from 21 to 26 mm. Their length is appropriately from 2 to 4 m.

Appropriately from an application point of view, the number of catalyst tubes accommodated in the tube bundle vessel is at least 5000, preferably at least 10 000. Frequently, the number of catalyst tubes accommodated in the reactor vessel is from 15 000 to 40 000. Tube bundle reactors having a number of catalyst tubes above 50 000 are usually exceptional. Within the vessel, the catalyst tubes are normally arranged in homogeneous distribution (preferably 6 equidistant neighboring tubes per catalyst tube), the distribution appropriately being selected such that the separation of the central internal axes of mutually adjacent catalyst tubes (the so-called catalyst tube pitch) is from 35 to 45 mm (cf., for example, EP-B 468290).

A particularly favorable heat exchange medium is the use of melts of salts such as potassium nitrate, potassium nitrite, sodium nitrite and/or sodium nitrate, or of low-melting metals such as sodium, mercury and alloys of different metals.

Charging of catalyst tubes in tube bundle reactors with catalysts obtainable in accordance with the invention is advantageous in particular when the tube bundle reactor is operated at an acrolein loading of the catalyst charge which is $\geq 135$ l(STP)/l·h, or $\geq 150$ l(STP)/l·h, or $\leq 160$ l(STP)/l·h, or $\geq 170$ l(STP)/l·h, or $\geq 180$ l(STP)/l·h, or $\geq 200$ l(STP)/l·h, or $\geq 220$ l(STP)/l·h, or $\geq 240$ l (STP)/l·h. It will be appreciated that such a catalyst charge is also advantageous at lower (e.g. $\leq 130$ l (STP)/l·h, or $\leq 100$ l (STP)/l·h, or $\leq 80$ l (STP)/l·h) acrolein loadings.

In general, the acrolein loading of the catalyst charge will, however, be $\leq 350$ l (STP)/l·h, or $\leq 300$ l (STP)/l·h, or $\leq 250$ l (STP)/l·h.

The volume-specific activity of the fixed catalyst bed will generally be configured such that it increases in flow direction of the reaction gas.

This can be realized in a simple manner, for example, by configuring the degree of dilution of the fixed catalyst bed with inert shaped bodies such that it decreases in flow direction of the reaction gas.

Otherwise, the heterogeneously catalyzed partial oxidation with coated catalysts obtainable in accordance with the invention can be performed in all aspects as detailed by DE-A 10350822. The acrolein content in the reaction gas input mixture may, for example, be at values of from 3 or 6 to 15% by volume, frequently from 4 or 6 to 10% by volume, or from 5 to 8% by volume (based in each case on the total volume).

The molar ratio of $O_2$:acrolein in the reaction gas input mixture will normally be $\geq 1$. Typically, this ratio will be at values of $\leq 3$. In many cases, the heterogeneously catalyzed acrolein partial oxidation to acrylic acid will be performed with an acrolein:oxygen:steam:inert gas volume ratio (I (STP)) present in the reaction gas input mixture of 1:(1 to 3):(0 to 20):(3 to 30), preferably of 1:(1 to 3):(0.5 to 10):(7 to 10).

Useful inert diluent gases include $N_2$, $CO_2$, CO, noble gases, propane, ethane, methane, butane and/or pentane (i.e., each as a sole diluent gas or in a mixture with another inert diluent gas or with a plurality of these other inert diluent gases). The reaction temperatures of such a heterogeneously catalyzed acrolein partial oxidation are typically in the range from 200 to 380° C., generally from 220 to 350° C., frequently from 245 to 285° C. or from 245 to 265° C. The working pressure is normally from 1 to 3 bar.

The acrolein conversion, based on single pass of the reaction gas mixture through the fixed catalyst bed, is typically $\geq 96$ mol %, frequently $\geq 98$ mol % and in many cases $\geq 99$ mol %.

In summary, the present application includes in particular (coated) catalysts which consist of a support body and a catalytically active composition applied to the surface of the support body, and also binders if appropriate, the catalytically active composition being a finely divided mixture of at least one finely divided multielement oxide comprising the elements Mo and V and at least one finely divided substance S selected from the group consisting of oxides of molybdenum and of compounds of molybdenum from which an oxide of molybdenum is formed under the action of elevated temperature and molecular oxygen.

Coated catalysts of the inventive type are suitable especially in heterogeneously catalyzed partial oxidations of acrolein to acrylic acid through an increased lifetime. In principle, they are, though, also suitable as catalysts for all other heterogeneously catalyzed partial oxidations detailed in EP-A 714700, DE-A 10350822 and WO 2004/108267, as catalysts with prolonged lifetime.

Catalysts obtainable by processes of the present invention are suitable especially for all partial oxidation and regeneration processes described in US 2006/0161019 (especially for the partial oxidations of acrolein to acrylic acid described there).

EXAMPLE AND COMPARATIVE EXAMPLE

1. Comparative Example

As described in Working Example 1 of WO 2004/108267, a multielement oxide composition of stoichiometry $Mo_{12}V_3W_{1.2}Cu_{2.4}O_x$ was prepared.

Figure 3:
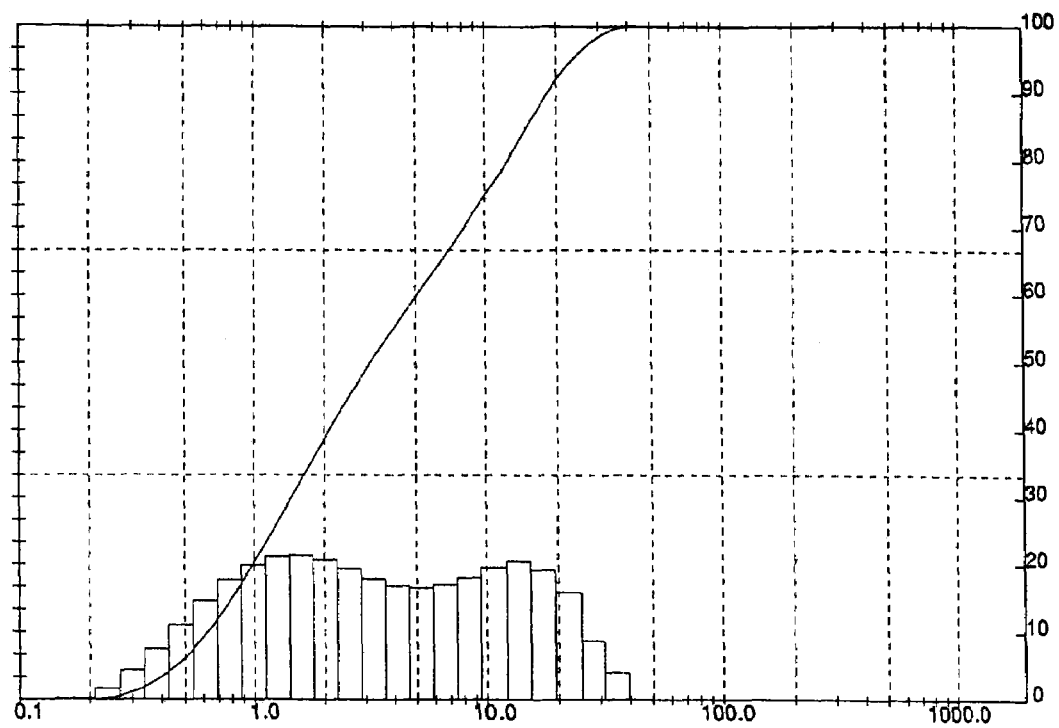
FIG. 3: Particle diameter distribution (volume fraction versus diameters (μm) on a logarithmic scale) for ground Mo12V3W1.2Cu2.4Ox.

The resulting catalytically active multielement oxide was ground by means of a biplex crossflow classifying mill (BQ 500) (from Hosokawa-Alpine Augsburg) to give a finely divided powder which had the particle diameter distribution shown in FIG. 3.

By means of the ground powder, as in Example Si of EP-A 714700, annular support bodies (external diameter 7 mm, length 3 mm, internal diameter 4 mm (7×3×4 mm), steatite C 220 from Ceram Tec with a surface roughness $R_Z$ of 62 μm, name: "Steatitring 7×3×4 porös beschichtet") were coated. As described in Example Si of EP-A 714700, the binder was an aqueous solution of 75% by weight of water and 25% by weight of glycerol. The active composition content of the resulting coated catalysts was, however, in contrast to the aforementioned Example S1, selected at 20% by weight (based on the total weight of support body and active composition). The quantitative ratio of powder and binder was adjusted proportionately. However, the further drying was not, as described in Example S1, effected in a tray oven at 250° C., but rather in a Memmert forced-air drying cabinet at 300° C. (2 h). A comparative coated catalyst CC1 was thus obtained.

2. Example

The procedure was as in the comparative example. However, the ground $Mo_{12}V_3W_{1.2}Cu_{2.4}O_x$ powder (400 g) was admixed with, based on the weight of the ground $Mo_{12}V_3W_{1.2}Cu_{2.4}O_x$ powder, 15% by weight of finely divided $MoO_3$ (60 g) ($MoO_3$ ("Molybdenum Trioxide I") from H. C. Starck, Mo content=66.6% by weight, $O_M$=1 m²/g, particle diameter distribution corresponding to FIG. 2).

Finally, the mixture was mixed homogeneously in a GT 550. Multimixer from Rotor Lips AG, CH-3661 Uetendorf, at level 8 over a period of 1 minute. The resulting finely divided mixture was used analogously to the comparative example to prepare an annular coated catalyst. However, the coating content was selected at 22.33% by weight (based on the total weight of support body and coating). The quantitative ratio of powder and binder was adjusted correspondingly. A working example coated catalyst WC1 was obtained.

3. Testing of Coated Catalysts CC1 and WC1

The coated catalysts were each tested as follows in a model catalyst tube flowed around by a salt bath (mixture of 53% by weight of potassium nitrate, 40% by weight of sodium nitrite and 7% by weight of sodium nitrate):

Model catalyst tube: V2A steel, wall thickness 2 mm, internal diameter 26 mm, a centered thermowell (for accommodating a thermoelement) of external diameter 4 mm, tube length 320 cm. After a preliminary bed of length 20 cm of inert rings (steatite C 220, 7×3×4 mm), the first 100 cm in flow direction were charged with a mixture of 70% by weight of the particular coated catalyst and 30% by weight of annular inert shaped bodies of steatite C 220 (external diameter 7 mm, length 3 mm, internal diameter 4 mm). The next 200 cm in flow direction were charged with the particular coated catalyst in undiluted form.

The reaction gas mixture had the following starting composition:
acrolein 4.4% by volume,
$O_2$ 5.4% by volume,
$H_2O$ 10.8% by volume,
CO 0.5% by volume,
$CO_2$ 0.9% by volume,
acrylic acid 0.4% by volume,
propylene 0.3% by volume and, as the remainder up to 100% by volume, $N_2$.

The acrolein loading of the fixed catalyst bed was set in each case to 90 l (STP)/l·h (the loading of a fixed catalyst bed catalyzing a reaction step with reaction gas or with a reaction gas component is understood to mean the amount of reaction gas or of reaction gas component in standard liters (=l(STP); the volume in liters that the corresponding amount of reaction gas or reaction gas component would take up under standard conditions, i.e. at 25° C. and 1 bar) which is conducted through one liter of fixed catalyst bed per hour).

The temperature of the salt bath was in each case adjusted such that the conversion of acrolein, based on a single pass of the reaction gas mixture through the fixed catalyst bed, was 99.6 mol % (the initial salt bath temperature required for this purpose, irrespective of the coated catalyst used, was 261° C.). The inlet temperature of the reaction gas mixture was adjusted to the particular salt bath temperature.

When coated catalyst WC1 was used, no increase in the salt bath temperature was required for this purpose over a run time of 58 days. The selectivity of acrylic acid formation over the entire run time was 94.8 mol %.

When coated catalyst CC1 was used, an increase in the salt bath temperature of 1° C. was required even over a run time of 54 days in order to balance out the accompanying catalyst deactivation and to maintain the acrolein conversion of 99.6 mol %.

U.S. Provisional Patent Application No. 60/829,419, filed Mar. 1, 2007, is incorporated into the present application by literature reference. With regard to the above-mentioned teachings, numerous changes and deviations from the present invention are possible. It can therefore be assumed that the invention, within the scope of the appended claims, can be performed differently from the way described specifically herein.

The invention claimed is:

1. A process for preparing a coated catalyst for counteracting deactivation of the catalyst, wherein the coated catalyst comprises a support body and a catalytically active composition, the process comprising:
preparing a finely divided mixture of
(i) at least one finely divided multielement oxide comprising elements Mo and V in a molar ration of Mo to V from 15:1 to 1:1, or comprising the elements Mo and V and in addition at least one of the two elements Te and Sb, and at least one element selected from the group consisting of Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In, and
(ii) at least one finely divided substance S selected from the group consisting of oxides of molybdenum and compounds of molybdenum selected from the group consisting of ammonium molybdate, ammonium polymolybdate, ammonium heptamolybdate tetrahydrate, molybdenum oxide hydrate, and molybdenum hydroxides from which an oxide of molybdenum is formed under an elevated temperature and molecular oxygen, wherein the oxide of molybdenum is a substance having a content of Mo and oxygen of at least 98 wt. %, and
applying the finely divided mixture as the catalytically active composition on the support body with the aid of a binder.

2. The process according to claim 1, wherein the finely divided substance S is $MoO_3$.

3. The process according to claim 1, wherein the specific surface area $O_M$ of the finely divided substance S is $\geq 0.1$ m$^2$/g and $\leq 5$ m$^2$/g.

4. The process according to claim 1, wherein a particle diameter $d_{50}$ of the finely divided substance S is $\geq 1$ μm and $\leq 200$ μm.

5. The process according to claim 1, wherein the active composition is applied to the surface of the support body in a layer thickness from 100 to 300 μm.

6. The process according to claim 1, wherein the active composition, based on the total amount of the finely divided multielement oxide comprising Mo and V, comprises >1 and <30% by weight of the finely divided substance S.

7. The process according to claim 1, wherein the binder is a solution composed of from 20 to 90% by weight of water and from 10 to 80% by weight of an organic compound.

8. A catalyst obtainable by a process according to claim 1.

9. A coated catalyst for counteracting deactivation of the catalyst, the coated catalyst comprising a support body and a catalytically active composition applied to the surface of the support body, and, optionally, one or more binder, wherein the catalytically active composition is a finely divided mixture of
(i) at least one finely divided multielement oxide comprising elements Mo and V in a molar ratio Mo:V from 15:1 to 1:1, or comprising the elements Mo and V and in addition at least one of the two elements Te and Sb and at least one element selected from the group consisting of Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In, and
(ii) at least one finely divided substance S selected from the group consisting of oxides of molybdenum and compounds of molybdenum selected from the group consisting of ammonium molybdate, ammonium polymolybdate, ammonium heptamolybdate tetrahydrate, molybdenum oxide hydrate, and molybdenum hydroxides from which an oxide of molybdenum is formed under an elevated temperature and molecular oxygen, wherein the oxide of molybdenum is a substance having a content of Mo and oxygen of at least 98 wt. %.

10. A process for heterogeneously catalyzed partial gas phase oxidation of acrolein to acrylic acid, comprising conducting the oxidation of acrolein to acrylic acid over the catalyst according to claim 8 or 9.

* * * * *